United States Patent [19]
Turner

[11] Patent Number: 5,822,887
[45] Date of Patent: Oct. 20, 1998

[54] OVER-THE-SHOE ATHLETIC SPAT

[76] Inventor: Gregory D. Turner, 5502 Tyler St., Sacramento, Calif. 95842

[21] Appl. No.: 870,437

[22] Filed: Jun. 6, 1997

Related U.S. Application Data

[63] Continuation-in-part of Ser. No. 647,210, May 9, 1996, abandoned, which is a continuation of Ser. No. 243,067, May 16, 1994, abandoned, which is a continuation of Ser. No. 81,418, Jun. 22, 1993, abandoned.

[51] Int. Cl.⁶ .............................. A43B 7/20; A43B 7/14; A61F 5/00
[52] U.S. Cl. ...................... 36/89; 36/88; 36/7.2; 36/132; 602/27
[58] Field of Search .................................. 36/7.1 R, 7.2, 36/7.3, 88, 89, 27, 132, 1.5, 2 R; 602/27

[56]   References Cited

U.S. PATENT DOCUMENTS

| | | | |
|---|---|---|---|
| 2,243,444 | 5/1941 | Sharp | 36/2 R |
| 2,260,138 | 10/1941 | Feinberg . | |
| 3,306,610 | 2/1967 | Biggs, Jr. et al. | 36/132 |
| 4,313,433 | 2/1982 | Cramer | 602/27 |
| 4,411,077 | 10/1983 | Slavitt . | |
| 4,604,816 | 8/1986 | Davison | 36/1.5 |
| 4,649,939 | 3/1987 | Curtis . | |
| 5,016,623 | 5/1991 | Krahenbuhl | 602/27 |
| 5,050,620 | 9/1991 | Cooper | 602/27 |
| 5,067,486 | 11/1991 | Hely | 602/27 |
| 5,090,138 | 2/1992 | Borden . | |
| 5,157,947 | 10/1992 | Parracho | 36/89 |

*Primary Examiner*—M. D. Patterson
*Attorney, Agent, or Firm*—Townsend and Townsend and Crew LLP

[57]    ABSTRACT

An ankle supporting spat according to the disclosed embodiment fits over the shoe of the wearer. A sole portion on the bottom of the spat overlaps the central portion of the shoe's sole. A top portion partially covers the shoe, ankle, and leg of the wearer, and is joined to the rand. The spat is open at both the heel and the toe so that the heel and the toe of the shoe protrude from the openings, exposing the front and rear cleats. A set of straps bind the spat to the wearer's shoe, ankle, and leg, and provide support for the ankle and other tissues. The particular amount, direction, and location of the support provided by the spat may be altered by changing the winding and arrangement of the straps.

6 Claims, 4 Drawing Sheets

OVER-THE-SHOE ATHLETIC SPAT

This Application is a continuation-in-part of application Ser. No. 08/647,210 filed May 9, 1996, now abandoned, which is a continuation of application Ser. No. 08/243,067 filed May 16, 1994, now abandoned, which is in turn a continuation of application Ser. No. 08/081,418 filed Jun. 22, 1993, now abandoned.

FIELD OF THE INVENTION

The invention relates to sports equipment, and more particularly, to equipment for supporting the ankle and foot of the athlete.

DESCRIPTION OF THE RELATED ART

Despite the health benefits of most athletic activities, most of them may be hazardous as well. Many sports, like football and basketball, severely stress the joints and tendons of the ankles, knees, and wrists, among other areas. Sports and activities requiring significant cutting and turning particularly strain the ankles of participants. Consequently, professionals and amateurs alike commonly suffer sprains, strains, and fractures of various joints, ligaments, tendons, and bones.

The ankle is one of the most vulnerable and frequently injured areas. Ankle injuries are commonly caused by the foot rolling under the ankle or twisting laterally with respect to the leg. These injuries are seldom irreparable, but usually require essentially immobilizing the ankle until the tissue mends, and may occasionally require surgery. The recovery process is painful and inconvenient, and imposes serious consequences on professional athletes whose careers depend on their health and ability to physically perform.

To reduce the severity of ankle injuries or prevent them altogether, many athletes wind tape around their ankles to form a tape spat. Several turns of adhesive tape are tightly bound around the ankle and around and under the foot, generally in a figure-eight pattern, leaving the heel and toe exposed. The specific method of wrapping the tape varies according to the needs and wishes of the athlete, because, inter alia, the particular technique for winding the tape in large measure determines the extent to which the various portions of the foot and ankle are supported y the tape spat. When the tape is in place, the tape spat provides significant support for the athlete's ankle and its associated ligaments, including the anterior and posterior ligaments. In particular, the tape spat supports the athlete's foot to prevent it from rolling, and resists excessive torsional movement of the foot as well.

Although tape usually provides effective support, large amounts of tape are required for each tape spat, and none of the used tape is recoverable. For professional sports teams in particular, supplying all of the players with tape for each game and practice session presents a significant expense. In addition, it is extremely difficult for an athlete to apply a tape spat to himself; hence, trainers are commonly required to wind the tape around the athlete's feet, ankles, and legs. Applying the tape is a lengthy and tedious process for both the athlete and the trainer, often requiring up to thirty minutes. Moreover, tape spats are usually applied immediately before a game or competition, during a time which could be used more productively by both the athlete and the trainer.

Another drawback of tape spatting surrounds its permanence; after the tape is applied, it cannot be conveniently adjusted without cutting the tape off and essentially starting over. As a result, if the tape becomes uncomfortable or otherwise hinders the athlete's performance, often the only practical options are to remove the tape until it can be reapplied or endure the discomfort or hindrance. In addition, when an athlete is injured, removing the tape spat is time consuming and painful, as it is difficult to immobilize the foot while the tape is removed.

Removing the tape presents yet another disadvantage. Tape spats are commonly removed with cutters that cut through the tape so that it may be peeled away from the athlete's shoe and leg. Cutting the tape, however, is imprecise and frequently cuts the wearer's shoe and sock as well. This mars the appearance and integrity of the shoe, and often destroys the shoe and sock altogether.

In addition, many athletes are called upon to perform under adverse conditions, such as mud, snow, and puddled water. The ankles and feet are particularly affected by such conditions, as they are constantly in contact with the muddy, frozen, or wet ground. Although tape spats may provide sufficient support for the ankle, they provide little or no protection from the elements. Consequently, some athletes may become more prone to various injuries and problems.

SUMMARY OF THE INVENTION

A foot of an athlete is reinforced at the ankle by the combination of an athletic shoe and a spat. The athletic shoe is conventional having a sole for contact with ground and attached heel, toe, and shoe top overlying and attached to the sole for supported confinement of the foot of an athlete—preferably an American Football shoe. The spat fits under the sole and over the shoe top. The spat includes a sole portion that fits over the sole between the sole and the ground. A spat top portion attaches to the sole portion that partially covers and fits over the ankle at the top and the sides of the athletic shoe. The spat top portion extends to the shoe adjacent the ankle of the wearer. Straps attach to the spat top portion and extend to a fastening disposition over the ankle of the athlete independent of shoe top for pulling on the sole portion in a stirrup like fashion. The straps pull upward on the sole portion and through the sole portion on the athletic shoe at the sole. This pulls the athletic shoe to the athlete's foot to reinforce the foot supporting confinement of the wearer's foot within the athletic shoe. Optionally, connection can be made between the spat and athletic show at the heel by hook and pile tape connecting between the spat and shoe. The process of reinforcing an athletic shoe is also set forth.

An athletic spat according to the present invention provides an over-the-shoe spat to support an athlete's ankle and foot. According to various aspects of the present invention, the spat: is wearable without the assistance of a trainer or other third party; requires no tape; may be donned by an athlete relatively quickly; is removable without the assistance of cutters; is reusable; is adjustable according to the athlete's comfort and needs; and is waterproof and thermally insulative. The spat suitably includes: a sole portion that fits across the sole of the shoe; a top portion that covers the top and sides of the shoe as well as the ankle and leg; a set of straps; and a mechanism for attaching the straps to the top portion and sole portion so that the straps may be wound around the ankle, shoe, and leg and firmly secured in position.

According to one aspect of the present invention, the subject spat is relatively easily donned by the athlete without the assistance of a trainer. The athlete slips his shoe and ankle into the spat, which expands to receive the shoe. The straps are suitably threaded through at least two pulleys to bind the spat to the shoe and ankle, and suitably secured with hook and loop tape. Because multiple windings of tape are not required, the athlete can apply the spat with minimal inconvenience and little or no assistance.

According to another aspect of the present invention, the spat may be removed without using cutters; rather, the straps are released from the spat and unwound. The spat is then simply slipped off the shoe, without marring the surface or otherwise damaging the shoe. The spat may then be stored for subsequent use as needed.

According to yet another aspect of the present invention, the subject spat may be conveniently adjusted by the athlete without removing the entire spat. If the spat becomes uncomfortable, the athlete can relatively quickly loosen and readjust the straps. Because multiple turns of tape are not involved, the spat may be adjusted rapidly and easily without completely removing the spat.

According to another aspect of the present invention, the spat is waterproof and thermally insulative to keep the ligaments and tendons of the ankle and foot warm. The top portion is suitably composed of a waterproof and insulative material, e.g., neoprene, which covers the shoe, ankle, and leg. In addition, the rand is likewise suitably composed of a durable, waterproof material. These materials protect the underlying shoe and ankle from outside water and other harsh conditions.

BRIEF DESCRIPTION OF THE DRAWING

A preferred exemplary embodiment of the present invention will hereinafter be described in conjunction with the appended drawing figures, wherein like designations denote like elements, and.

DETAILED DESCRIPTION OF A PREFERRED EXEMPLARY EMBODIMENT

Figure 1:
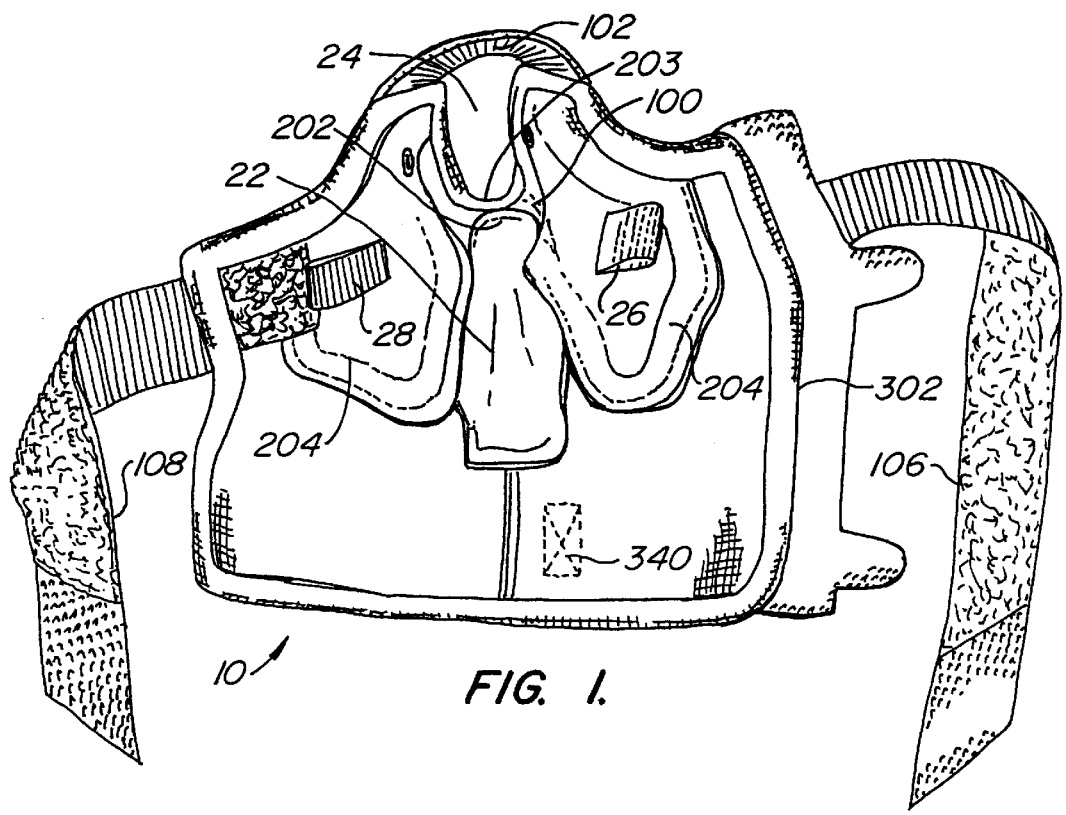
FIG. 1 is a perspective view of the spat of this invention looking from the side of the spat which contacts the shoe with upper central aperture through which the toe of the athletic fits being shown above the lower central aperture through which the heel of the athletic shoe fits.

Referring now to FIG. 1, exemplary over-the-shoe athletic spat 10 according to the present invention is suitably configured to fit over shoe 12, ankle (not visible in FIG. 1), and leg 14 of a wearer to support the ankle and surrounding tissues, including the posterior and anterior ligaments. In the illustrated embodiment, shoe 12 suitably includes heel 16, toe 18, and respective front cleats 20a and rear cleats 20b. Spat 10 suitably extends upwardly along leg 14 of the wearer, for example to the bottom of the wearer's calf.

Spat 10 suitably comprises: rand 100 configured to be positioned against the bottom of shoe 12; flexible top portion 102 configured to generally surround the wearer's ankle, leg 14 and the top and sides of shoe 12; and a plurality of strap 106 and strap 108 extending from spat 10 and configured to be wrapped around the ankle and over the top of shoe 12 and spat 10.

Spat 10 is illustratively open at heel 16 (see opening 22 on FIG. 1) allowing shoe 12 to project through the rear and bottom of spat 10. Spat 10 is also illustratively has opening 24 at toe 18 so that toe 18 of shoe 12 extends forwardly through the opening. Shoe 12 is advantageously disposed within spat 10 such that a snug fit is maintained between toe position 18 and the forward opening of spat 10. In the preferred embodiment, the bottom of spat 10 is positioned just behind respective cleats 20a projecting from sole of shoe 12.

It is necessary to pull with some considerable force athletic spat 10 over toe 18 of shoe 12. To assist this, right pull loop 26 and left pull loop 28 are provided on the inside of athletic spat 10. By pulling on these respective loops 26, 28, and inserting toe 18 of shoe 12 through opening 24, athletic spat 10 fits over toe 18 of the shoe.

In the preferred embodiment, sole portion 100 is not detachable. Sole portion 100 is suitably composed of a flexible, lightweight, and durable material, and may be somewhat elastic to effectively conform to the shape of the wearer's shoe 12 and provide optimal fit. For example, sole portion 100 may be composed of rubber or a synthetic material, e.g., HERCULITE".

sole portion 100 suitably comprises front portion 203 and heel portion 202, including opening 22 disposed to permit heel 16 of shoe 12 to extend therethrough. Opening 22 is suitably large enough to permit sole portion 100 to grasp the outermost surface of heel 16 of shoe 12, and to grasp the midportion of shoe 12 in front of rear cleats 20b of shoe 12. The front edge of sole portion 100 suitably comprises a substantially straight line so that the portion of sole portion 100 in contact with the underside of shoe 12 extends transversely across the bottom of shoe 12.

The portion of sole portion 100 overlapping the back of the wearer's shoe 12 suitably extends upward to approximately the level of the wearer's ankle. This portion of sole portion 100 also suitably includes cushioning material 204, e.g., air pillows or foam, to add firm support at the back of the foot.

Respective downwardly projecting spikes may be formed in the material of sole portion 100, for example on the undersurface of the portion of sole portion 100 in the vicinity of the bottom of shoe 12, for added traction. Other features and finishes may be applied to sole portion 100 to provide traction suited to particular types of terrain, such as artificial turf or sod.

Referring now to FIGS. 2–7, top portion 102 of spat 10 covers much of the top and sides of shoe 12, and surrounds the lower portion of the wearer's leg 14. Top portion 102 is suitably composed of a flexible lightweight material which conforms to the shape of the wearer's shoe 12 and leg 14. Top portion 102 is suitably composed of an insulative material, for example neoprene, to provide thermal insulation for the foot and leg 14. Top portion 102 is further suitably waterproof to keep the wearer's foot, shoe 12, and leg 14 substantially isolated from the elements. Thermal insulation and waterproofing provided by top portion 102 protect the wearer from the elements and help keep the tissues warm, thus reducing the risk of injury.

Figure 2:
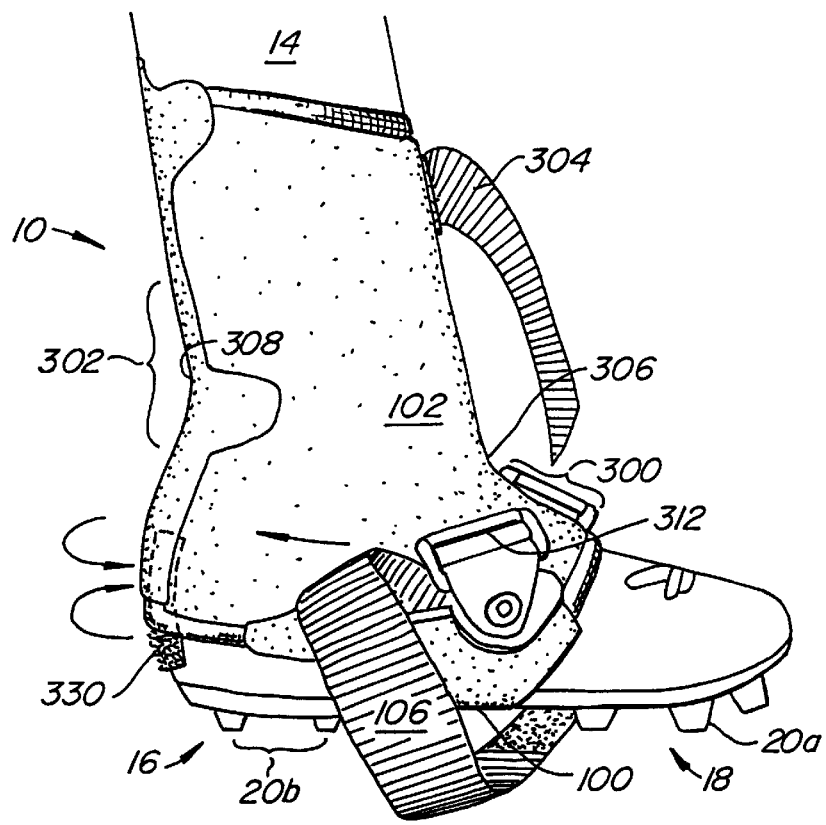
FIG. 2 is a side elevation perspective of the shoe and spat after the toe portion of the spat has been inserted and the back portion of the spat fastened about the ankle of the wearer.
Figure 3:
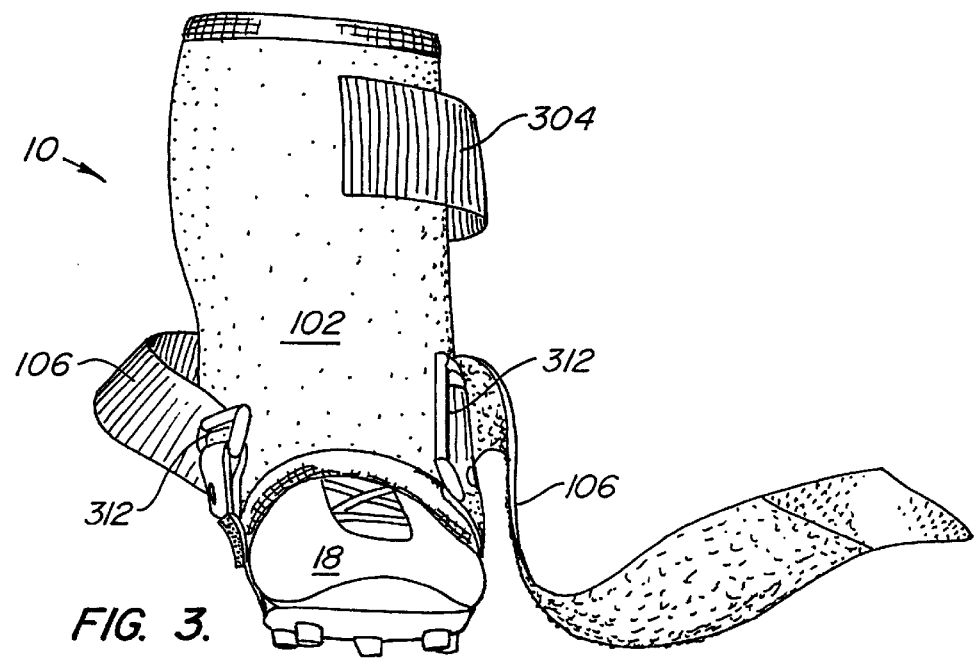
FIG. 3 is a view of the spat of FIG. 2 taken from in front of the toe portion of the shoe illustrating the first strap being wrapped around the back of the ankle.
Figure 4:
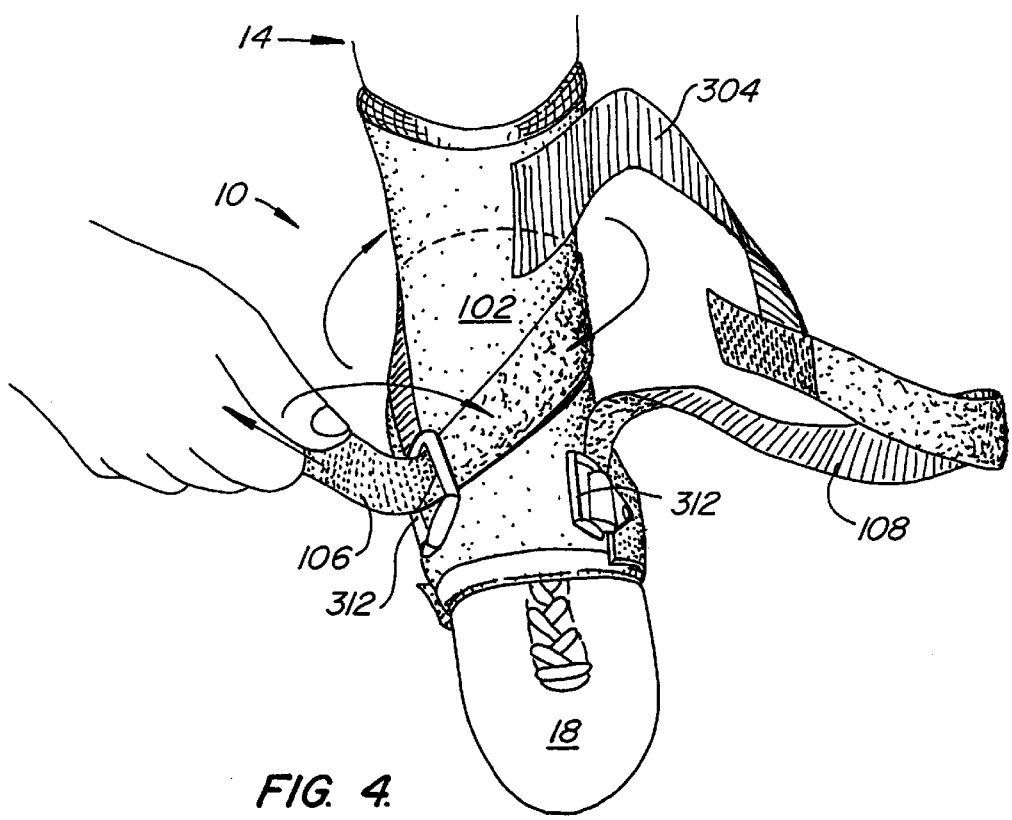
FIG. 4 is a view of the spat of FIG. 3 illustrating the tightening of the strap on one side of the shoe.
Figure 5:
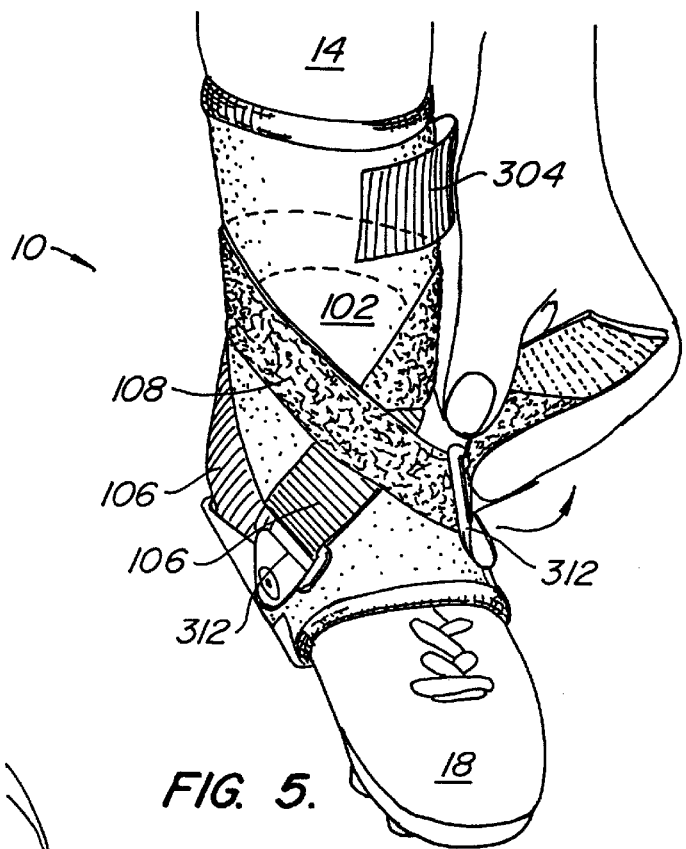
FIG. 5 is a view of the spat of FIG. 4 illustrating the tightening of the strap on the opposite side of the spat.

Referring to FIG. 2, top portion 102 suitably comprises front portion 300, creases 306, trim band 304, and strap channel 308. Top portion 102 is attached to rand 100 along their common edges, suitably by stitching (e.g., a nylon material) to provide a strong and durable bond between top portion 102 and sole portion 100. Front portion 300 of top portion 102 is attached to the edges of sole portion 100. Toe 18 of shoe 12 extends through the loop formed opening 24, advantageously facilitating a substantially water resistant seal against shoe 12.

The material of top portion 102 is cut to match the general shape of leg 14 and shoe 12 to provide a close fit. Back 302 of top portion 102, configured to snugly contact the back of leg 14 and the back of shoe 12, is suitably composed of continuous (e.g., seamless) material for optimal waterproofing and strength. The upper edge of top portion 102 is suitably trimmed with a durable and flexible band 304, suitably rubber, to protect the edge from damage and provide a relatively snug, water resistant seal against the wearer's leg.

A set of creases or wrinkles 306 may be formed in top portion 102 at the front of spat 10 where shoe 12 and leg 14 of the wearer meet. Creases 306 facilitate the bending of spat 10 in response to changes in angle between shoe 12 and leg 14, for example due to running or walking. Creases 306 advantageously facilitate a walking or running motion, but resist against shoe 12 rolling from underneath the ankle or torsional twisting of shoe 12 with respect to leg 14.

Top portion 102 may also include cushioning material 204 formed in or attached to the sides of top portion 102, for example surrounding the ankle or other appropriate areas of the wearer. Cushioning material 204 is suitably formed of air pockets or foam material inserted in proper locations to add support near or around the ankle or other sensitive areas.

With continued reference to FIG. 2, back 302 of top portion 102 above heel 16 suitably includes a strap channel 308 formed in the fabric of top portion 102. Strap channel 308 can suitably comprises parallel slits formed in top portion 102. If parallel strips are used, a strap may be threaded through strap channel to guide the strap around the back of shoe 12 and leg 14, and to prevent the strap from slipping from its proper position. It should be noted, however, that strap channel is optional, and it is contemplated that strap channel 308 may be omitted without significantly detracting from the performance of spat 10.

It will be understood that the top of spat 10 suitably comprises a continuous web of material, or, alternatively, respective segments of material joined (e.g., stitched). With this configuration, spat 10 may slide over shoe 12 much like a sock slides over a foot.

Referring to FIGS. 1 and 2, to don spat 10, shoe 12 is inserted through opening 24 substantially circular top portion of spat 10 towards toe 18.

As shown in FIG. 2, toe 18 of shoe 12 extends through the front opening of spat 10 until the front edge 203 of rand 100 is positioned behind front cleats 20a of shoe 12. Similarly, heel 16 of shoe 12 extends through opening 22 in rand 100 so that heel 16 of shoe 12 is exposed.

The length of rand 100 is suitably designed to fit between the front cleats 20a and the rear cleats 20b for the particular shoe. In the event spat 10 is used with a cleat pattern other than shown in FIG. 1, the length of rand 100 may be configured to be disposed between the front cleats and rear cleats of such cleat pattern.

Alternatively, small openings may be formed in rand 100 through which one or more of respective cleats 20a, b may extend. Such openings are suitably trimmed with a substantially rigid (e.g., aluminum) ring to protect the edges of the openings. The openings may be positioned to correspond to cleat locations that would otherwise be covered by rand 100. Thus, spat 10 may be configured to accommodate a broad array of cleat patterns.

After shoe 12 and leg 14 are inserted into spat 10, spat 10 is secured to the wearer using a plurality, suitably two as in the exemplary embodiment, of straps 106, 108. Strap 106 is suitably secured to top portion 102, preferably on the outside, and overlaps the top of spat 10. Toe strap 106 is wound behind back 302 and then looped through strap pulley 312. After strap 106 is threaded through strap pulley 312, toe strap 106 is pulled taut to secure spat 10, folded back over the top of spat 10, and secured in any suitable manner, e.g., with hook and loop tape, such as Velcro. Strap 106 is shown fastened to the inside of what is the left foot of an athlete.

Second strap 108, also secured to top portion 102 or sole portion 100 of spat 10, is suitably wrapped over spat 10 and around leg 14 and the ankle to provide support. Second strap 108 is suitably permanently attached, e.g., stitched, to sole portion 100 or top portion 102, or may be removably attached to top portion 102 or sole portion 100, for example, by hook and loop tape. Second strap 108 may be threaded through strap pulley 312 or an additional strap pulley secured to top portion 102 or sole portion 100 but further away from toe 18 than first strap pulley.

When strap 108 is pulled tight, sole portion 100 suitably operates like a stirrup, pulling shoe 12 to the wearer's foot. If strap 108 is tightened sufficiently through strap pulley 312, sole portion 100 suitably raises rand 100 towards the arch of wearer's foot, which tends to move wearer's weight to the balls of the feet. This is an added advantage for athletes that run on the balls of their feet.

Second strap 108 may be wrapped around leg 14 and shoe 12 according to the wearer's needs and desires. Suitably, second strap 108 is wrapped around the ankle, across top portion 102, and through pulley 312 in a modified figure-eight pattern to support ankle. The particular method of wrapping may be varied to change the particular location and directions of support provided to wearer.

Figure 6:
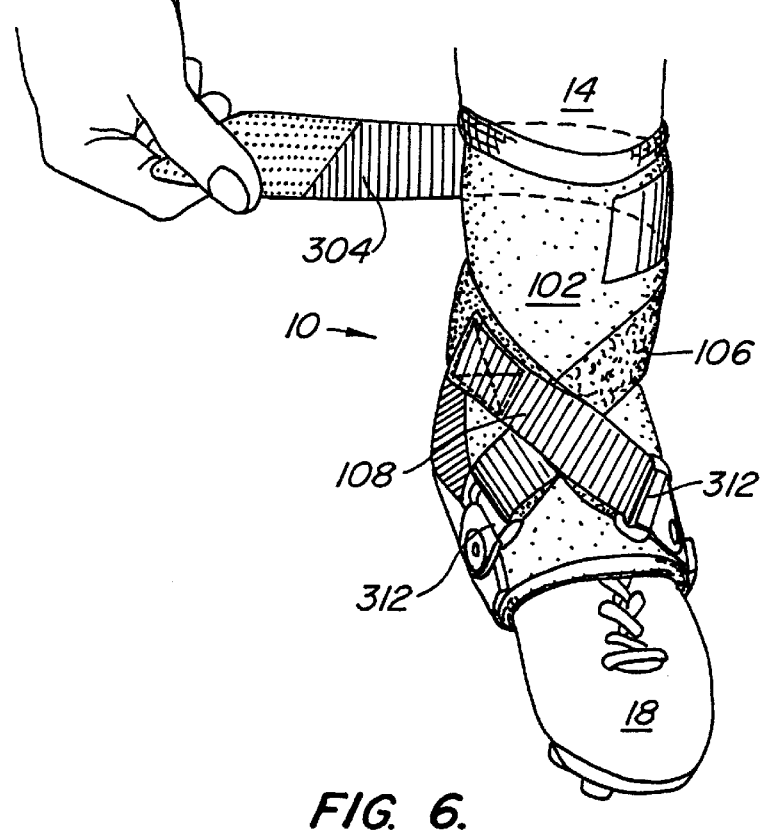
FIG. 6 is a view of the spat of FIG. 5 illustrating the wrapping of the spat at the top of the ankle supporting portion of the spat; and, FIG. 7 illustrates completed fastening of the spat to the shoe.
Figure 7:
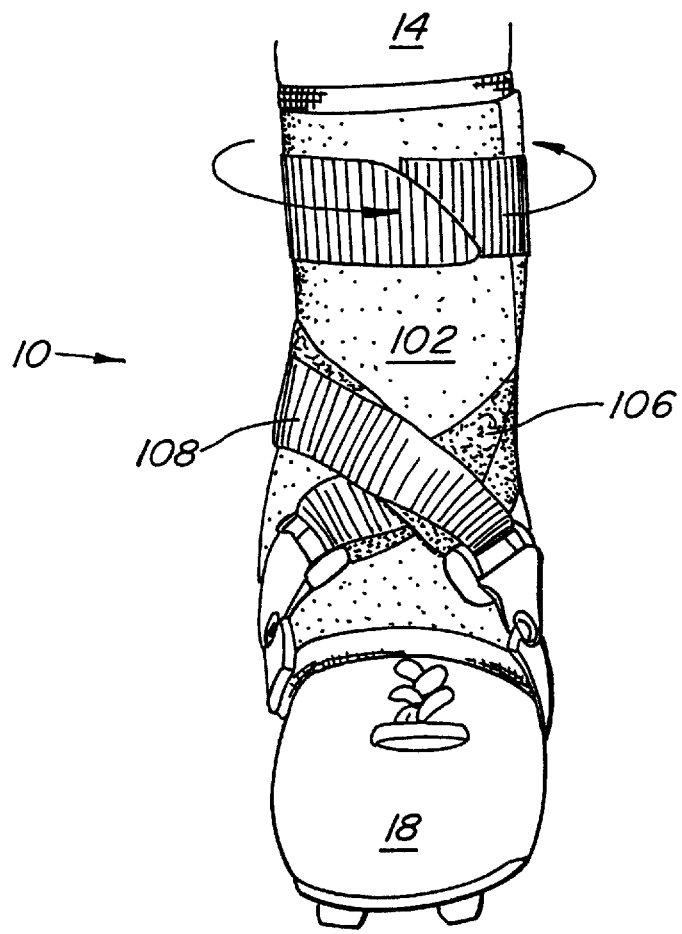

Finally, and once straps 106, 108 are in place, strap 304 is wound at the top of athletic spat 10. This much is illustrated at FIGS. 6 and 7.

It is sometimes important to key heel 16 of shoe 12 to the corresponding portion of flexible top portion 102 that fits over heel 16. This can be done by adhesive hook tape 330 and pile tape 340 sewn on the inside of athletic spat 10 at the portion contacting heel 16.

An athletic spat according to the present invention provides a more convenient and faster method of applying spatting than conventional tape spatting. A spat according to the present invention provides the wearer with support around the ankle and foot without the assistance of a trainer or other party. In addition, because the spat does not require multiple windings of tape, the spat may be put on and taken off relatively quickly. Because no tape is required, costs incurred due to wrapping the foot and leg with tape are no longer incurred. In addition, a spat according to the present invention is easily removed and does not require cutting; thus the danger of destroying or damaging shoes by the cutters is eliminated.

It should be understood that while various aspects and designs are shown in the drawing, they are not so shown in the limiting sense and variations are well within the skill of one of ordinary skill in the art. It should also be noted that the colors and construction of a spat according to the present invention may vary to conform to the dress code requirements of various athletic leagues or team uniforms. In addition, the present invention is not limited solely to shoes, but may be applied in conjunction with skates, boots and similar footwear as well. Similarly, materials, features, designs, and construction are exemplary only, and various changes and substitutions may be made from those shown in the drawing figures without departing from the spirit of the invention as set forth in the following claims.

What is claimed is:

1. The combination of a shoe and shoe support over a foot of an athlete comprising:

an athletic shoe having a sole for contact with ground and attached heel, toe, and ankle supporting shoe top overlying and attached to the sole for supported confinement of the foot of an athlete;

a spat for fitting under the sole and over the ankle supporting shoe top including;

a sole portion that fits over the sole between the sole and the ground;

a spat top portion attached to the sole portion that partially covers and fits over the ankle supporting top and sides of the athletic shoe, the spat top portion extending to the ankle supporting shoe adjacent the ankle of the wearer;

straps attached to the spat top portion and extending to a fastening disposition over the ankle of the athlete independent of ankle supporting shoe top for pulling on the sole portion in a stirrup like fashion, for pulling upward on the sole portion and through the sole portion on the athletic shoe at the sole to pull the athletic shoe to the athlete's foot to reinforce the foot supporting confinement of the wearer's foot within the athletic shoe.

2. The combination of a shoe and shoe support over a foot of an athlete according to claim 1 and further including:

the athletic shoe includes cleats attached to the sole and depending to the ground; and, the sole portion defines holes for extending around the cleats while in contact with the sole of the athletic shoe.

3. A process of reinforcing the foot of an athlete in an athletic shoe comprising the steps of:

placing the foot of the athlete in an athletic shoe having a sole for contact with ground and attached heel, toe, and ankle supporting shoe top overlying and attached to the sole for supported confinement of the foot of an athlete;

conventionally tightening the foot of the athlete within the athletic shoe;

providing a spat for fitting under the sole and over the ankle supporting shoe top including;

a sole portion that fits over the sole between the sole and the ground;

a spat top portion attached to the sole portion that partially covers and fits over the ankle supporting top and sides of the athletic shoe, the spat top portion extending to the ankle supporting shoe adjacent the ankle of the wearer;

straps attached to the spat top portion and extending to a fastening disposition over the ankle of the athlete independent of ankle supporting shoe top;

placing the sole portion under the sole of the athletic shoe;

wrapping the spat top portion over the ankle supporting top and sides of the athletic shoe;

pulling on the sole portion through the straps in a stirrup like fashion, for pulling upward on the sole portion and through the sole portion on the athletic shoe at the sole to pull the athletic shoe to the athlete's foot to reinforce the foot supporting confinement of the wearer's foot within the athletic shoe; and, fastening the straps to the a foot of the wearer independent of the athletic shoe to further reinforce the foot of the athlete within the athletic shoe.

4. A process of reinforcing the foot of an athlete in an athletic shoe according to claim 3 and wherein:

providing cleats on the athletic shoe;

providing holes corresponding to the cleats in the sole portion to enable the rand to contact the sole of the athletic shoe around the cleats; and, fitting the rand over the shoe with the cleats extending through the holes in the sole portion.

5. The combination of a shoe and shoe support over a foot of an athlete comprising:

an athletic shoe having a sole for contact with ground and attached heel, toe, and ankle supporting shoe top overlying and attached to the sole for supported confinement of the foot of an athlete;

a spat for fitting under the sole and over the ankle supporting shoe top including;

a sole portion that fits over the sole between the sole and the ground;

a spat top portion attached to the sole portion that partially covers and fits over the ankle supporting top and sides of the athletic shoe, the spat top portion extending to the ankle supporting shoe adjacent the ankle of the wearer;

straps attached to the spat top portion and extending to a fastening disposition over the ankle of the athlete independent of ankle supporting shoe top for pulling on the sole portion in a stirrup like fashion, for pulling upward on the sole portion and through the rand on the athletic shoe at the sole to pull the athletic shoe to the athlete's foot to reinforce the foot supporting confinement of the wearer's foot within the athletic shoe; and, a tape attached to a heel of the shoe; and, means attached to the spat for adhering to the tape on the heal of the shoe.

6. The combination of a shoe and shoe support over a foot of an athlete according to claim 5 and further including:

the athletic shoe includes cleats attached to the sole and depending to the ground; and, the sole portion defines holes for extending around the cleats while in contact with the sole of the athletic shoe.

* * * * *